(12) United States Patent
Ikegami et al.

(10) Patent No.: US 8,100,980 B2
(45) Date of Patent: Jan. 24, 2012

(54) ARTIFICIAL ELBOW JOINT

(75) Inventors: Hiroyasu Ikegami, Maguro-ku (JP);
Yukio Horiuchi, Koto-ku (JP);
Shinichiro Takayama, Minato-ku (JP);
Shigeki Momohara, Bunkyo-ku (JP);
Atsuhito Seki, Bunkyo-ku (JP);
Toshiyasu Nakamura, Shinjuku-ku (JP); Atsushi Tanji, Kawasaki (JP);
Keitaro Yamamoto, Okayama (JP)

(73) Assignee: Nakashima Propeller Co., Ltd., Okayama (JP)

( * ) Notice: Subject to any disclaimer, the term of this patent is extended or adjusted under 35 U.S.C. 154(b) by 147 days.

(21) Appl. No.: 11/921,212

(22) PCT Filed: May 10, 2006

(86) PCT No.: PCT/JP2006/309973
§ 371 (c)(1),
(2), (4) Date: Nov. 28, 2007

(87) PCT Pub. No.: WO2006/129495
PCT Pub. Date: Dec. 7, 2006

(65) Prior Publication Data
US 2009/0105839 A1    Apr. 23, 2009

(30) Foreign Application Priority Data

May 31, 2005    (JP) ................................. 2005-159047

(51) Int. Cl.
*A61F 2/42*    (2006.01)
(52) U.S. Cl. ................. 623/20.11; 623/20.12; 623/19.14
(58) Field of Classification Search ............... 623/19.14, 623/20.11, 20.12, 20.13
See application file for complete search history.

(56) References Cited

U.S. PATENT DOCUMENTS

| | | | | |
|---|---|---|---|---|
| 3,708,805 A | * | 1/1973 | Scales et al. | ............... 623/20.12 |
| 4,538,306 A | | 9/1985 | Dorre et al. | |
| 6,379,387 B1 | * | 4/2002 | Tornier | ...................... 623/20.12 |
| 2004/0186580 A1 | * | 9/2004 | Steinmann | ................. 623/20.11 |

FOREIGN PATENT DOCUMENTS

| | | |
|---|---|---|
| CH | 541 963 | 11/1973 |
| CH | 541963 | 11/1973 |
| EP | 0 575 107 | 12/1993 |
| JP | 54-132391 | 10/1979 |
| JP | 01-236049 | 9/1989 |
| JP | 09-511668 | 11/1997 |
| JP | 2000-107209 | 4/2000 |
| JP | 2000-217852 | 8/2000 |
| JP | 2000-342610 | 12/2000 |
| JP | 2004-351209 | 12/2004 |

* cited by examiner

*Primary Examiner* — David Isabella
*Assistant Examiner* — Joshua Levine
(74) *Attorney, Agent, or Firm* — DLA Piper LLP (US)

(57) ABSTRACT

An artificial elbow joint including a humeral component made of metal and an ulnar component made of resins for replacing an elbow joint. The humeral component of this artificial elbow joint is configured by a substantially cylindrical trochlea and a stem extending from the trochlea that is inserted into the humeral; and the ulnar component is configured by a joint surface member which receives the trochlea of humeral component in a rotatable manner and a stem which extends from the joint surface member and is inserted into the ulna. The stem of the humeral component is curved gently downward overall so as to comply with the lordotic shape of the humeral, and the trochlea is turnable about the centerline of the stem.

5 Claims, 8 Drawing Sheets

ARTIFICIAL ELBOW JOINT

TECHNICAL FIELD

This present invention relates to an artificial elbow joint for replacing an elbow joint.

BACKGROUND TECHNOLOGY

When the joint function of an elbow joint is lost due to rheumatism, rheumatoid arthritis, external injury or the like, replacement with an artificial elbow joint is performed in the interest of greater quality of life. In such an artificial elbow joint, conventionally, stems of the artificial elbow joint are inserted in the humeral and in the ulna and coupled together with a bendable mechanism in a separable manner as seen in Patent Literature 1. In this artificial elbow joint, the two stems must be inserted at the same time into the humeral and ulna. For this reason, the surgery is difficult; and since no rotational function is involved, the artificial elbow joint is functionally inferior to the biological joint.

In view of the above, such an artificial elbow joint as seen in Patent Literature 2 is proposed. In this artificial elbow joint, a substantially cylindrical trochlea and a joint surface member that has a concave curved surface for rotatably receiving the trochlea are prepared separately, and the stems of these elements are inserted into the humeral and the ulna, respectively. In the humeral side component of this prior example, the stem is made straight in shape and is inserted inside the humeral. However, the anatomical shape of the humeral is made so that the diaphyseal part at the distal end is hollowed out on the lower surface side (which is the lower surface side when the palm is extended face up) in what is called the olecranon fossa, and the entirety of the humeral curves (protrudes) gently downward (such a shape is called a "lordotic shape"). As a result, the stem of the humeral side component becomes exposed at the olecranon fossa, and sufficient support strength cannot be obtained. For that reason, what has been done is to form a concavity inside the trochlea which is at the base of the stem, so that the distal end of the humeral is sandwiched by the concavity to supplement the support strength. However, in this structure, the bone must be cut to make the distal end to conform to the shape of the concavity, adding difficulty to the surgery, and placing a great deal of burden on the patient.

Furthermore, the joint surface of the ulna side component and the stem extending from the joint surface are all made of a medical resins (a super-macromolecular polyethylene), and the stem is inserted in the ulna and secured by cement. However, these components are low in strength due to the properties of the material and inferior in terms of support strength, and they also would cause micromotion (which is repetition of minute motions when a force is applied and the component itself deforms), damaging the bone in the periphery of the stem. As a result, because both the humeral component and the ulnar component have weak support strength, loosening occurs in the course of use, requiring re-surgeries or the like.

Patent Literature 1: Japanese Patent Application Laid-Open No. 54 (1979)-132391
Patent Literature 2: Japanese Patent Application Laid-Open No. 2000-107209

DISCLOSURE OF INVENTION

Problems the Invention Attempts to Solve

The present invention provides an artificial elbow joint that has a long-term stability with the impartation of a prescribed support strength augmenting structure in both the humeral component and the ulnar component.

Means for Resolving Problems

Given the problem described above, the present invention, as described in claim 1, provides an artificial elbow joint that is for replacing an elbow joint, and it comprises a humeral component made of metal and an ulnar component made of resins, wherein the humeral component is configured by a substantially cylindrical trochlea and a stem that extends from the trochlea and is inserted in the humeral, the ulnar component is configured by a joint surface for rotatably receiving the trochlea of the humeral component and a stem that extends from the joint surface and is inserted into the ulna, and wherein the stem of the humeral component is curved gently downward so as to comply with the lordotic shape of the humeral, and the trochlea is made turnable about the center axis of the stem.

Furthermore, the present invention, as described in claim 2, provides a means in which the stem of the ulnar component is made of metal and is formed with a receptacle at the tip thereof for receiving substantially the entire area of the joint surface, and through-hole(s) is provided in the receptacle for a screw(s) that can be screwed into the cortical bone of the ulna; and, as described in claim 3, provides a means in which through-hole(s) is provided in the stem of the ulnar component for a screw(s) that can be screwed into the ulna; and further, as described in claim 4, provides a means in which the stem of the ulnar component is tapered when seen in the plan view and is curved gently downward when seen in the side elevational view and is also formed to be tapered.

ADVANTAGES OF THE INVENTION

According the means of claim 1, the humeral component is formed so that the stem thereof follows the lordotic shape of the humeral having no longer an exposed portion; as a result, it has an increased medullary cavity occupation ratio with an intraspinal holding strength. Also, because the trochlea is substantially cylindrical, it needs only be mounted by being imbedded in the epiphysis of the humeral, and no special bone cutting demanding a high level of skill is required. In addition, because the trochlea can turn about the centerline of the stem, it is possible to eliminate the difficulty of being unable to adjust the angle of the trochlea associated with the fact that the attitude wherein the stem of the humeral component is imbedded inside the medullary cavity is specifically determined by the shape described earlier. Accordingly, the surgery can be performed simply and in a short time, and the burden on the patient can be reduced.

According to the means of claim 2, moreover, since the stem is made of a metal that exhibits high strength in the ulnar component also, no micro-motion or the like is caused to occur, the support strength thereof is strong, and the securing strength is further increased when emplacing a screw(s). According to the means of claim 3, furthermore, it is possible to further enhance the ulnar component's securing strength; and according to the means of claim 4, since the stem of the ulnar component accords with the shape of the ulna, the medullary cavity occupation ratio becomes high, and since the joint surface is received by the receptacle, there is no insufficiency in strength.

EXPLANATION OF THE SYMBOLS 1 humeral component
2 trochlea
2a insertion hole
2b screw hole
3 stem
3a insertion part
3b hollowed out channel
4 humeral
4a medullary cavity
5 ulnar component
6 joint surface member
7 stem
7a receptacle
8 ulna
8a medullary cavity
8b cortical bone
9 screw
10 insertion passage hole
11 set screw
12 radius

BEST MODES FOR CARRYING OUT THE INVENTION

Figure 1:
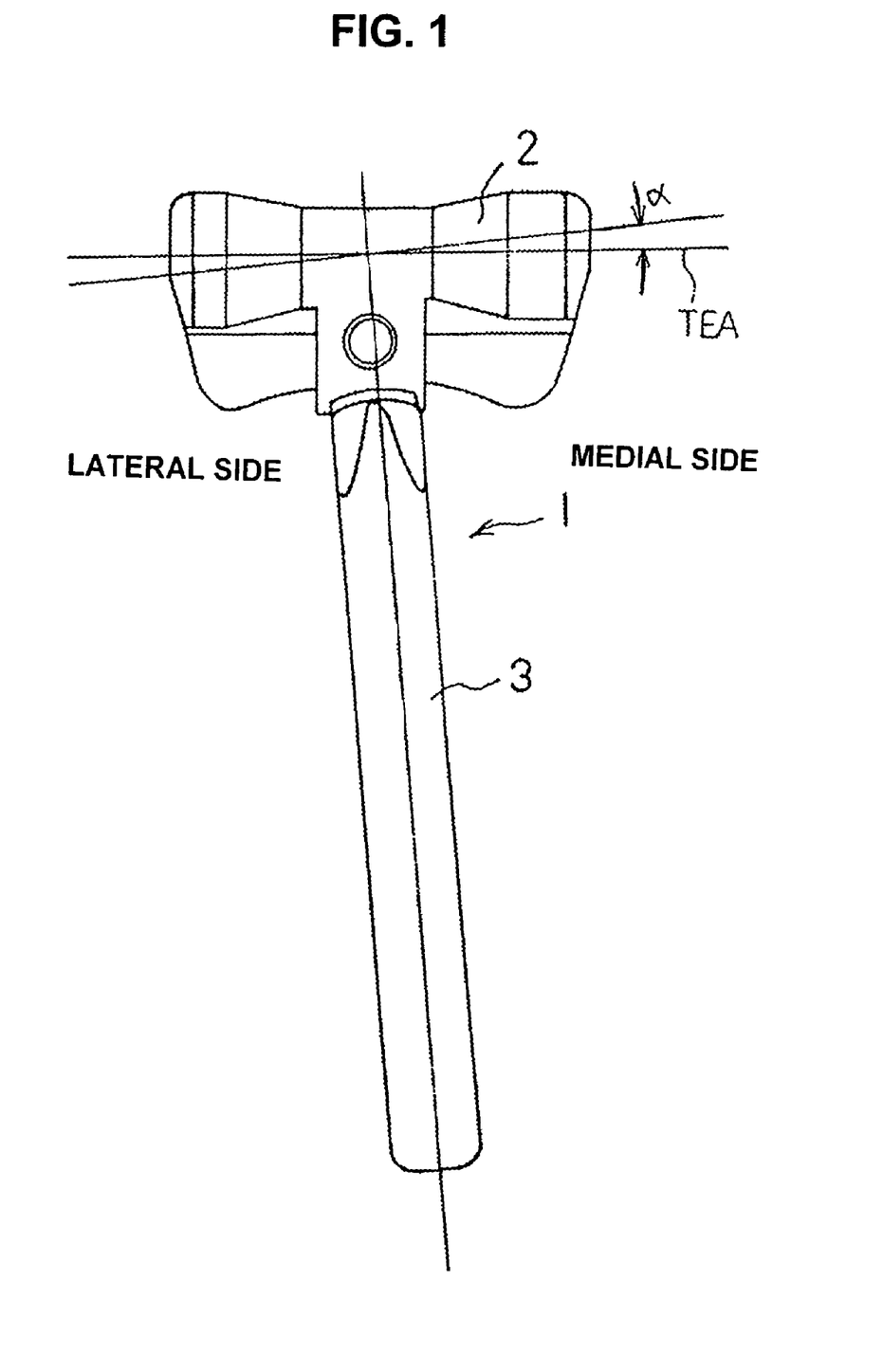
FIG. 1 is a top plan view of a humeral component according to the present invention.
Figure 2:
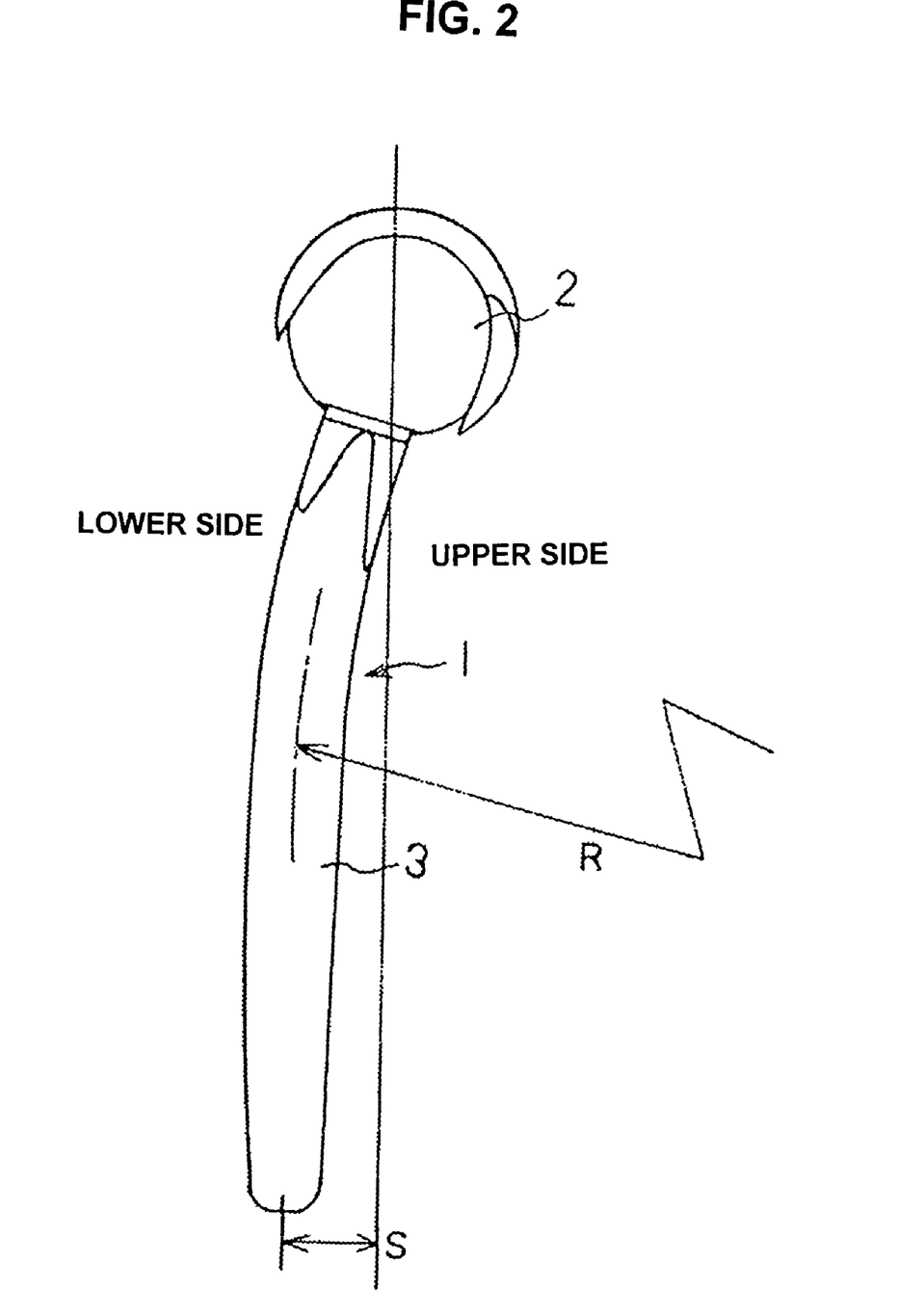
FIG. 2 is a side elevational view of the humeral component.

Embodiments of the present invention will be now described below with reference to the drawings. FIG. 1 is a top plan view of a humeral component 1, while FIG. 2 is a side elevational view thereof. The humeral component 1 is comprised of a trochlea 2 and a stem 3. The trochlea 2 provides a joint function with the joint surface of an ulnar component that will be described subsequently, and it is made either of a metal compatible with the human body, such as a titanium alloy, cobalt chrome molybdenum alloy, or stainless steel alloy or the like, or of a medical ceramic or the like. The trochlea 2 is formed in a substantially cylindrical shape, and its middle portion is in a hollowed-out drum shape like that of the trochlea of a biological elbow joint. The positions and directions referred to in the description below are based on the configuration of the arm in which the humeral and ulna are extended with the palm facing upward.

The stem 3 of the humeral component 1 is made of the same material as that of the trochlea 2, and it is a tail piece that extends outwardly from the center of the trochlea 2. Here, the stem 3 is straight when seen in a top plan view, and it is of substantially the same width throughout its entire length; however, the center axis (TEA (transepicondylar axis)) of the trochlea 2 is made to inclined toward the body side of the patient by an outer half angle α (4 to 6° or so) with respect to a line that is perpendicular to the center axis of the stem 3; as a result, the stem 3 can be accommodated inside the medullary cavity 4a along the axis of the humeral 4. Contrariwise, while the width of the stem is the same for the entire length when seen in the side elevational view, the stem is made to gently curve downward so as likewise to be accommodated inside the medullary cavity 4a. Though the radius of curvature R of that curve depends on the size of the stem, it is 400 to 700 mm, with the amount of the offset S between the center of the trochlea 2 and the end of the stem 3 being set to be 6 to 9 mm.

Figure 3:
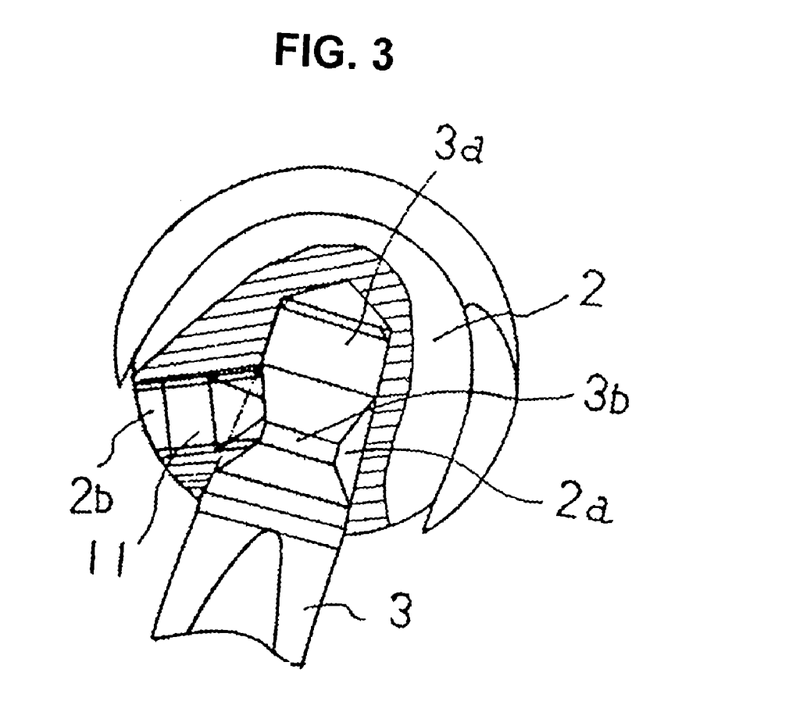
FIG. 3 is a partially sectional view of the main portion of the attachment between the trochlea and the stem of the humeral component.
Figure 4:
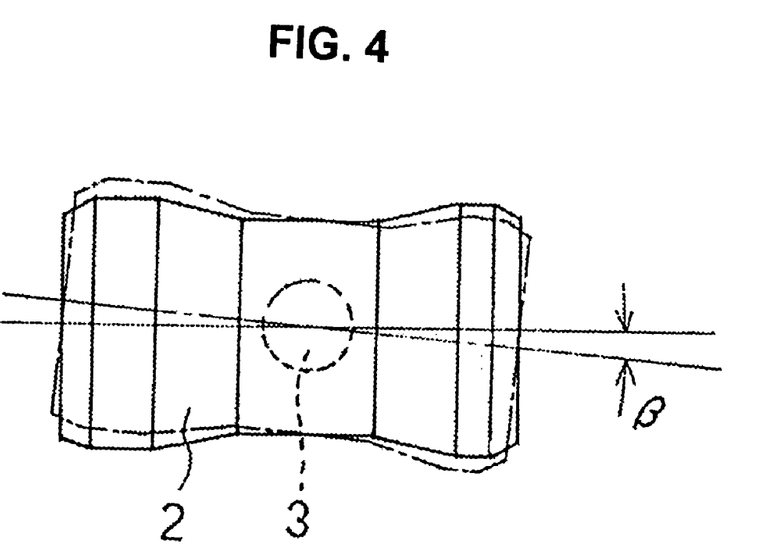
FIG. 4 is a front elevational view of the trochlea of the humeral component.

FIG. 3 is a cross-sectional view of the main portion that makes the connection between the trochlea 2 and the stem 3 of the humeral component 1. FIG. 4 is a front elevational view of the trochlea 2. An insertion part 3a that is tapered so as to be thinner towards the tip end is formed at the tip end of the stem 3, and a hollowed out channel 3b that is hollowed out from the outer circumference is formed midway along the insertion part 3a. In the trochlea 2 on the other hand, an insertion hole 2a is formed so that the insertion part 3a of the stem 3 is inserted therein, and also a screw hole 2b is formed in the trochlea 2 so that it extends toward the insertion hole 2a. With this structure, the insertion part 3a of the stem 3 is inserted into the insertion hole 2a of the trochlea 2, and a set screw 11 is screwed into the screw hole 2b to secure the stem 3 therein in such a manner that the trochlea 2 is turnable about the center axis of the stem 3 and thus the angle of the trochlea is adjustable. Accordingly, the inclination of the TEA (central axis) of the trochlea 2 with respect to a horizontal plane passing through the center of the stem 3, that is, the angle of rotation β, can be set freely. In the present invention, the stem 3 is not straight, and it rather curves in a vertical direction (see FIG. 2); as a result, the rotational attitude of the stem 3 with respect to the medullary cavity 4a is specifically established (since the stem is curved in a vertical direction)

Figure 5:
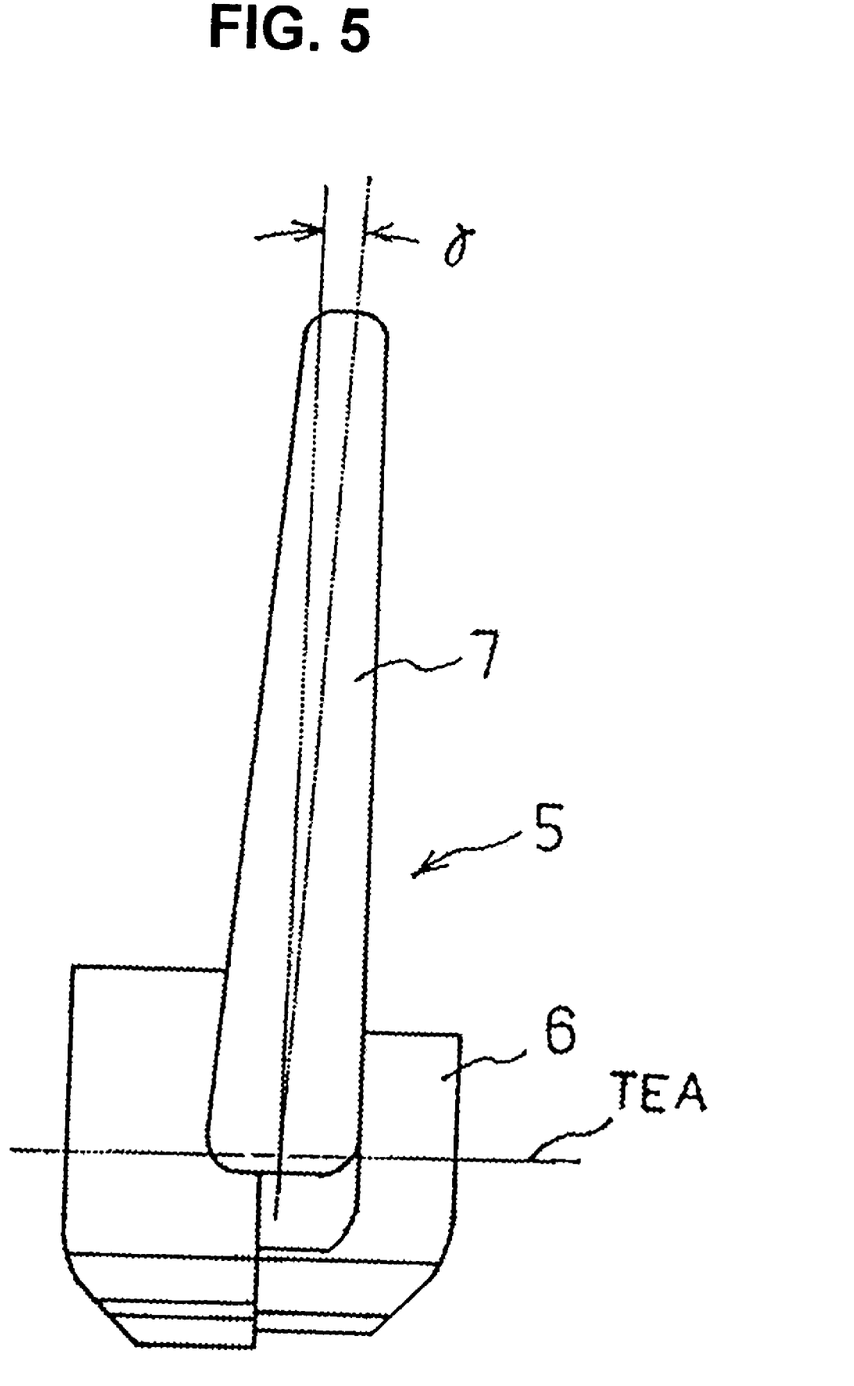
FIG. 5 is a top plan view of an ulnar component according to the present invention.
Figure 6:
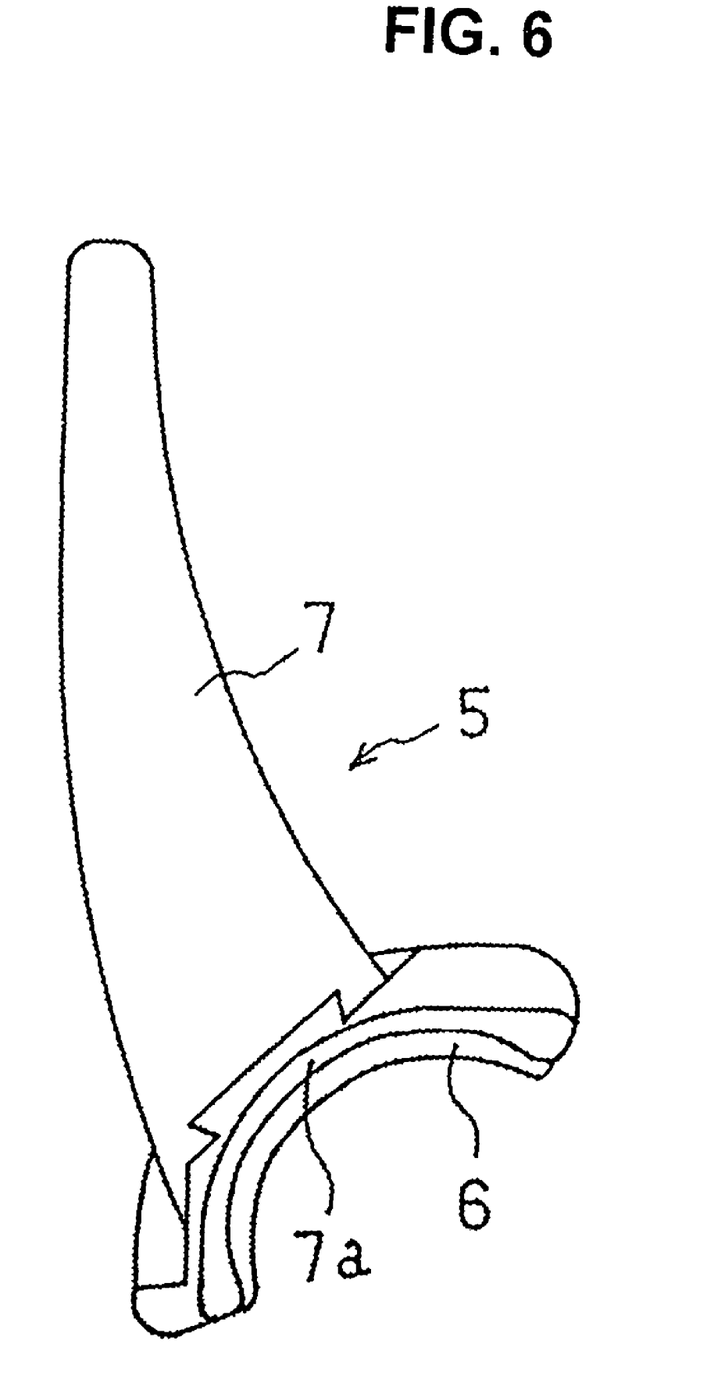
FIG. 6 is a side elevational view of the ulnar component.

FIG. 5 is a top plan view of an ulnar component 5, and FIG. 6 is a side elevational view thereof. The ulnar component 5 is comprised of a joint surface member 6 and a stem 7. The joint surface member 6 is provided so as to face the trochlea 2 of the humeral component; and it has, in the center part thereof, a shallow concave surface that is substantially half-cylindrical in shape so that it can rotate on the trochlea 2. The joint surface member 6 is made of a medical resins that is a super-macromolecular polyethylene or the like having good sliding properties against metals. With this structure, the trochlea 2 of the humeral component and the joint surface member 6 of the ulnar component 6 turn at the contact surfaces thereof, so that bending and extending motions of the elbow can be made, with slight rotational motions being allowed, thus exhibiting the same functions as a biological elbow joint.

The stem 7 of the ulnar component 5 has a receptacle 7a formed at the tip end thereof so that it accepts substantially the entire area of the outer surface of the joint surface member 6. In the present invention, the stem 7 is made of the same metal as the humeral component 1. The stem 7 in the shown embodiment is tapered when seen in the top plan view and is likewise inclined toward the patient's body by an angle γ (4 to 6° or so) with respect to the normal line of the TEA, so that the stem can be accommodated inside the medullary cavity 8a of the ulna 8. Furthermore, when seen from the same side view, the stem is formed to gently curve downward and is tapered so that it is accommodated inside the medullary cavity 8a. In addition, the surfaces of the humeral component 1 and ulnar component 5 described above which make contact with bones are formed to have the porosity of a porous material or mesh or the like to enhance the bondability with the bones as the bones grow.

Figure 7:
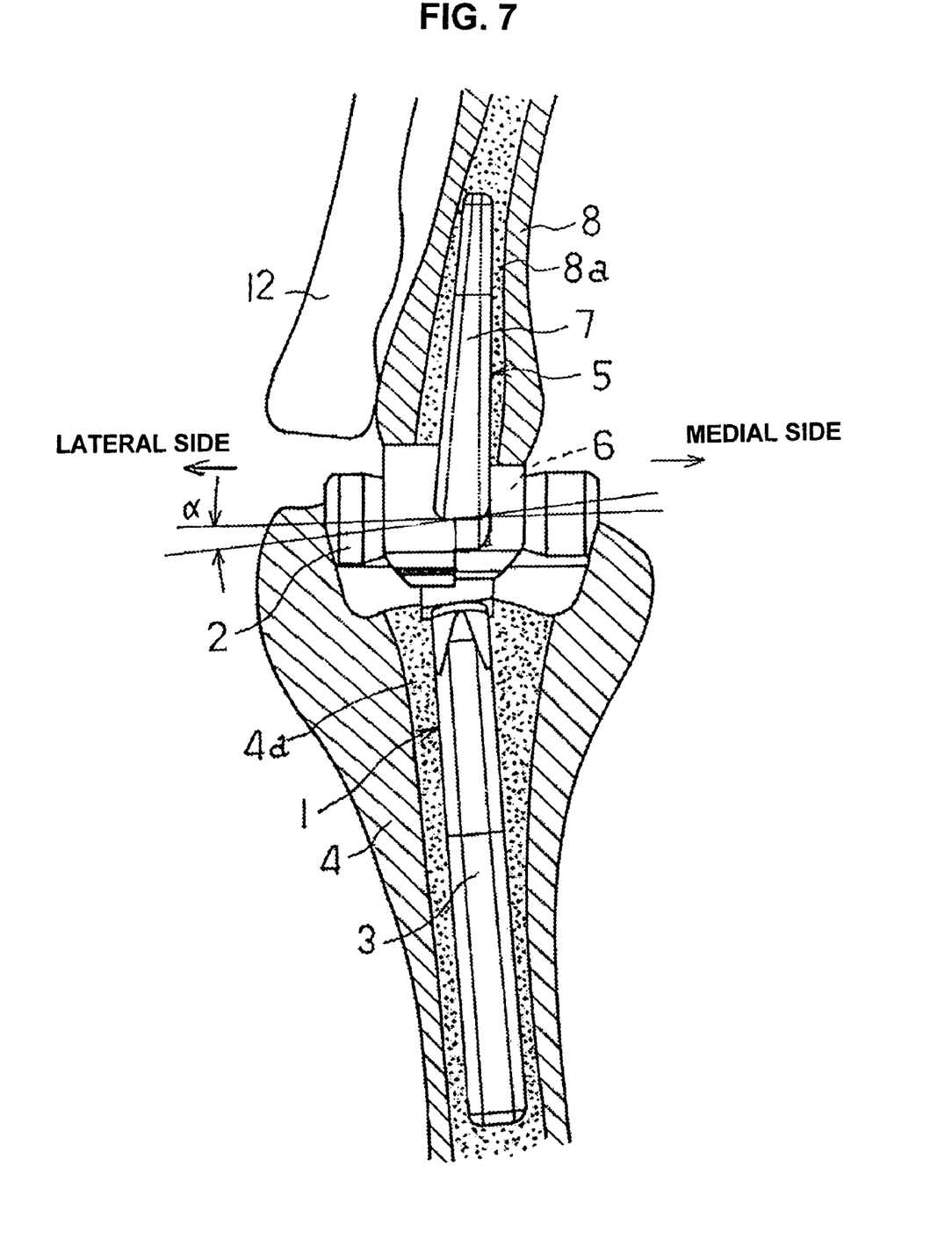
FIG. 7 is a sectional top plan view of a left arm in which the elbow joint is replaced by the artificial elbow joint of the present invention.

FIG. 7 is a cross-sectional top plan view of a left arm of a patient with the elbow joint replaced by the artificial elbow joint of the configuration described above, while FIG. 8 is a cross-sectional side elevational view thereof. In the humeral 4, the distal end extends away from the body of the patient, while the distal end of the ulna 8 extends and is curved so as to be closer to the patient body. Here, when mounting the humeral component 1, the bone at the distal end of the humeral 4 is cut so that the trochlea 2 of the humeral component 1 is accommodated in the same position as the trochlea of the biological elbow joint, and the stem 3 of the humeral component 1 is inserted inside the medullary cavity 4a of the humeral 4 to effect the mounting. As a result, the TEA, as in the biological elbow joint, is inclined by the angle α noted earlier with respect to the bone axis. In the artificial elbow joint of the present invention, moreover, only the humeral 4 and the ulna 8 are joined as joint elements, and the radius 12 is not part of the joint elements. This is because the ulna 8 and the radius 12 are joined together with ligament tissue; and thus, if the ulna 8 is caused to effect bending and extending motions, the radius 12 is also moved in linkage with the ulna.

Figure 8:
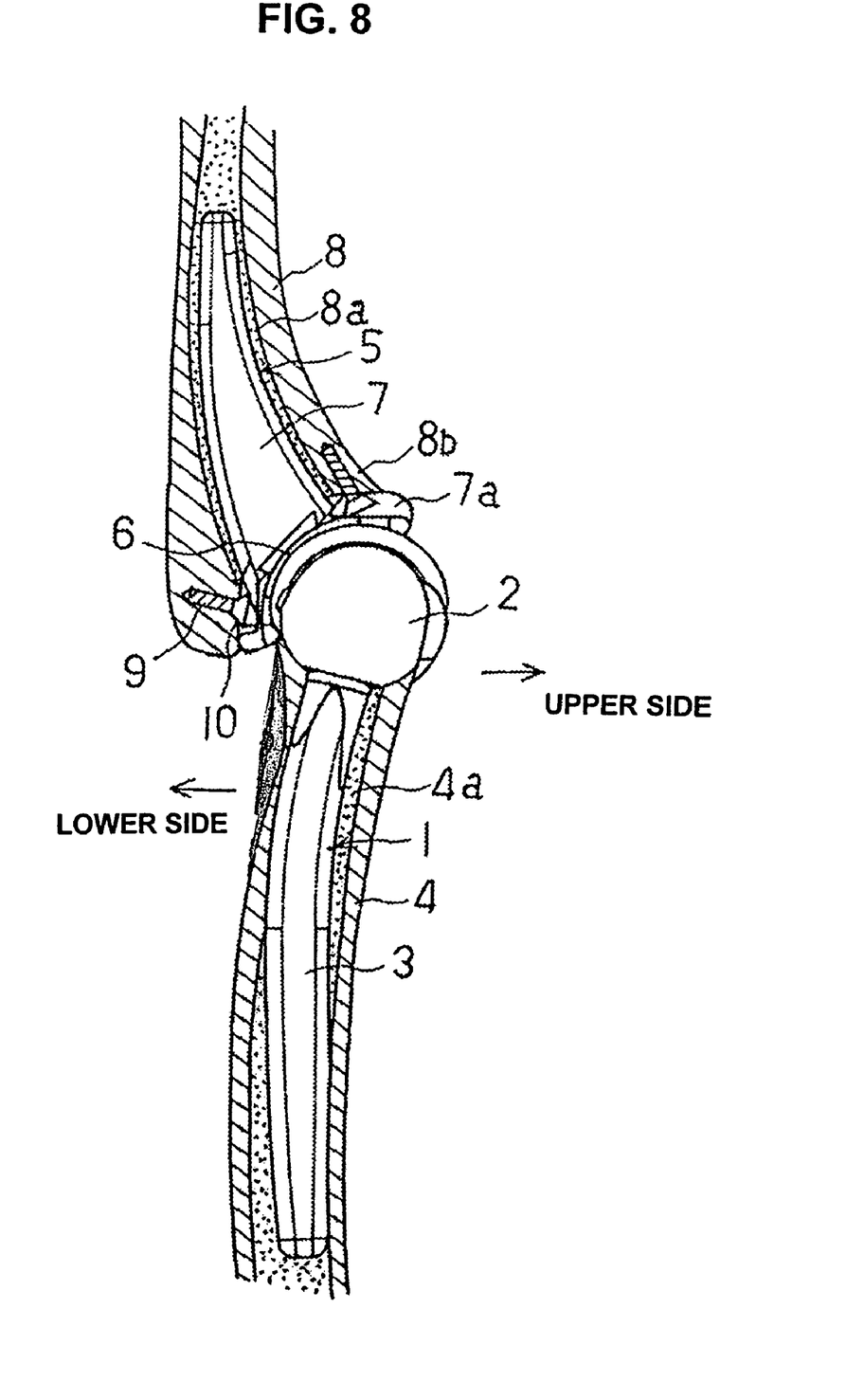
FIG. 8 is a sectional side plan view of a left arm in which the elbow joint is replaced by the artificial elbow joint of the present invention.

The ulnar component 5 is mounted in a similar manner to the humeral component. More specifically, the stem 7 of the ulnar component is inserted into the medullary cavity 8a from the proximal end side of the ulna 8, and the joint surface member 6 of the ulnar component 5 is placed so as to slide against the trochlea 2 of the humeral component 1. Moreover, when the TEA of the ulnar component is inclined by the angle γ as described earlier with respect to the bone axis, the stem 7 of the ulnar component is oriented slightly toward the outside from the axis of the ulna 8. Since the inward curvature of the ulna 8, when seen in the top plan view, is comparatively large, the stem 7 of the ulnar component 5 is made shorter than the stem 3 of the humeral component 1; and, in conjunction therewith, with such a design of the ulnar component, it is possible to insert the stem 7 of the ulnar component in as close to the center of the ulna 8 as possible In the manner of the mounting as described above, when mounting the humeral component 1 and the ulnar component 5, there is no particular necessity to use bone cement or the like which is thought to adversely affect the human tissue. In addition to what has been described above, with a screw (flat screw) 9 screwed from the receptacle 7a of the ulnar component 5 toward the cortical bone 8b of the ulna 8, the securing strength of the ulnar component 5 on the cortical bone is made even stronger. In particular, in view of the fact that the medullary cavities of patients suffering from rheumatism exhibit severe degrees of damage, and almost no securing strength can be expected, this method provides a great deal of benefit.

For the reason described above, insertion passage hole(s) 10 for allowing the screws 9 to pass therethrough are provided in the receptacle 7a of the ulnar component. Though the number of screws 9 is not particularly limited, it is preferable that screws can be screwed in at two or more locations on the upper and lower sides of the receptacle. In addition, while not shown in the drawings, it is also possible that the screw(s) 9 be inserted from the joint surface 6 side to pass through the receptacle 7a and screwed into the cortical bone 8b. In this structure, not only is provided an effect of the screw or screws 9 securing the joint surface 6 and the receptacle 7a together, but also the added advantages that the securing strength is enhanced and cement is made unnecessary is obtained.

Figure 9:
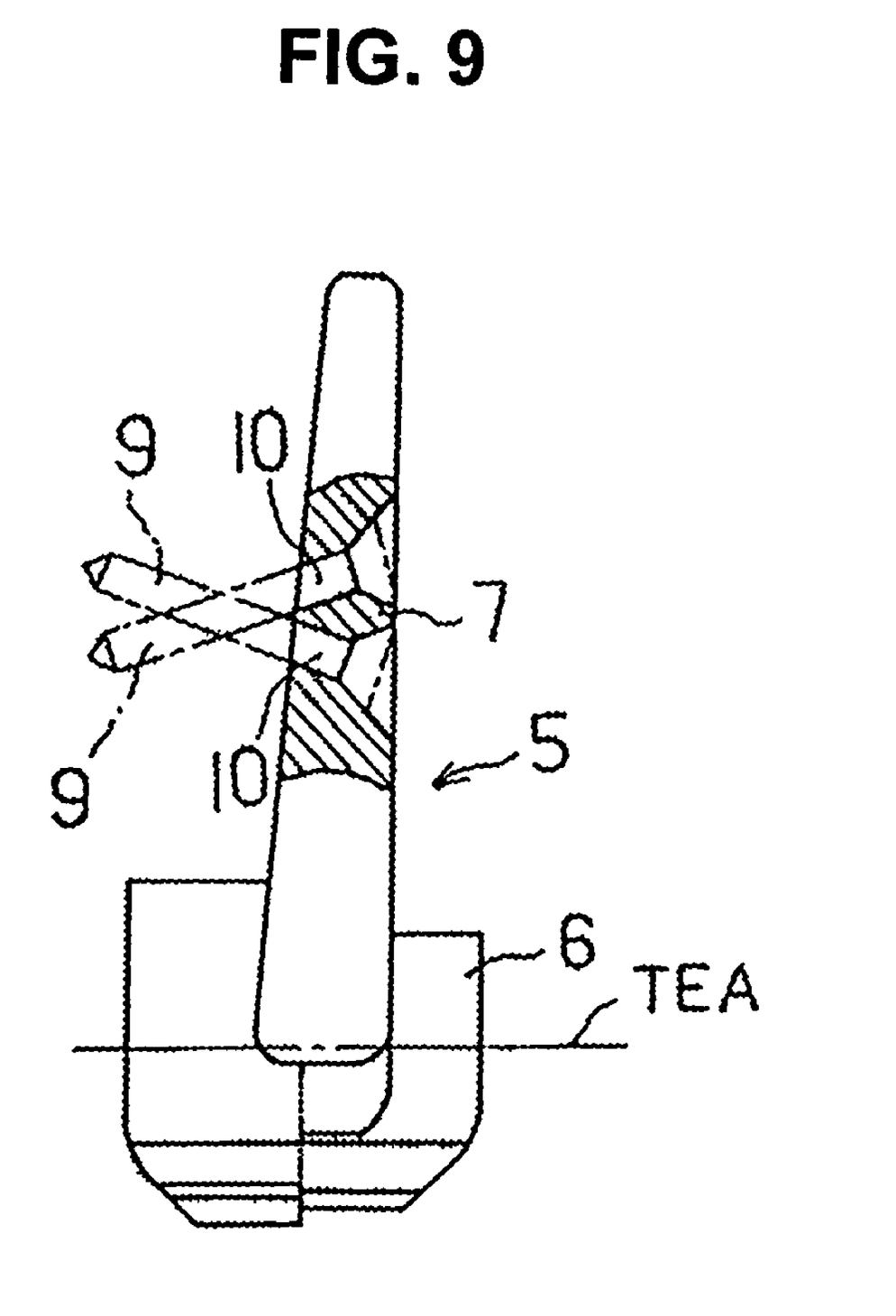
FIG. 9 is a partially sectional top plan view of another example of an ulnar component according to the present invention.

FIG. 9 is a partially cross-sectional top plan view of another example of the ulnar component 5 of the present invention. In this example, screw holes 10 for screws 9 are formed in the stem 7 of the ulnar component, and screws 9 are passed through the screw holes 10 and screwed into the ulna 8 to enhance the securing strength. In this structure, though any number of screws 9 can be used, at least two or more should be used, and it is preferable in the interest of enhanced securing strength that the screws 9 be screwed in so as to cross each other (the angle of such crossing being not specified). Moreover, when the ulna 8 is brittle, then such a method can be employed that screw holes are provided in the stem 7 and screws 9 are screwed into the stem 7 from the ulna 8 side.

The invention claimed is:

1. An artificial elbow joint for replacing an elbow joint, comprising:
   a humeral component made of metal; and
   an ulnar component made of resins; wherein
   the humeral component is comprised of a substantially cylindrical trochlea and a stem that extends from said trochlea and is inserted in a humerus;
   the ulnar component is comprised of a joint surface member that faces the trochlea and a stem that extends from said joint surface member and is inserted into an ulna, said joint surface member facing said trochlea being provided in a center part thereof with a shallow concave surface which is substantially half-cylindrical in shape so as to rotatably contact a surface of the substantially cylindrical trochlea while being unconstrained thereto;
   the stem of the humeral component, when seen in a top plan view, is provided to incline so that the interior angle becomes acute with respect to a centerline of the trochlea, and when seen in a side elevational view, is made to curved gently downward so as to comply with a lordotic shape of the humerus; and
   the trochlea is provided so as to be turnable about a center longitudinal axis of the stem, so that an angle with respect to a horizontal plane passing through the centerline is adjusted and fixed.

2. The artificial elbow joint according to claim 1, wherein the stem of the ulnar component is made of metal;
   a receptacle is formed at a tip end of the stem for receiving substantially an entire area of the joint surface member; and
   a through-hole is formed in the receptacle for a screw that is screwed into a cortical bone of the ulna.

3. The artificial elbow joint according to claim 1 or 2, wherein a through-hole is provided in the stem of the ulnar component for a screw that is screwed into the ulna.

4. The artificial elbow joint according to any one of claims 1 to 3, wherein the stem of the ulnar component is tapered when seen in a top plan view, is curved gently downward when seen in a side elevational view, and is formed so as to be tapered.

5. An artificial elbow joint according to claim 1, wherein the stem of the humeral component includes an insertion part at one end;
   the trochlea is provided with an insertion hole into which said insertion part of said humeral component is inserted;
   the trochlea is provided with a screw hole extending therethrough to said insertion hole and a screw is screwed into said screw hole to engage with said insertion part of said humeral component; and
   whereby said trochlea is turnable about the center axis of said stem of said humeral component and an angle of said trochlea is adjusted and fixed.

* * * * *